United States Patent
Harada

(10) Patent No.: US 7,955,860 B2
(45) Date of Patent: Jun. 7, 2011

(54) METHOD OF DETECTING RESIDUAL DETERGENT AND DEVICE FOR DETECTING RESIDUAL DETERGENT

(75) Inventor: Shiro Harada, Fukuoka (JP)

(73) Assignee: Lumica Corporation, Koga (JP)

( * ) Notice: Subject to any disclaimer, the term of this patent is extended or adjusted under 35 U.S.C. 154(b) by 128 days.

(21) Appl. No.: 12/293,028

(22) PCT Filed: Dec. 29, 2006

(86) PCT No.: PCT/JP2006/326295
§ 371 (c)(1),
(2), (4) Date: Mar. 20, 2009

(87) PCT Pub. No.: WO2007/077941
PCT Pub. Date: Jul. 12, 2007

(65) Prior Publication Data
US 2009/0325308 A1    Dec. 31, 2009

(30) Foreign Application Priority Data
Jan. 6, 2006    (JP) .................................. 2006-001001

(51) Int. Cl.
*G01N 21/76*    (2006.01)
(52) U.S. Cl. ................ 436/172; 435/4; 422/50; 422/52; 422/68.1
(58) Field of Classification Search .......... None
See application file for complete search history.

(56) References Cited

U.S. PATENT DOCUMENTS
4,756,410 A    7/1988    Hildebrandt et al.

FOREIGN PATENT DOCUMENTS
| JP | 63-096071 A | 4/1988 |
| JP | 1993-49675 U | 6/1993 |
| JP | 5-232026 A | 9/1993 |
| JP | 8-313443 A | 11/1996 |
| JP | 8-320315 A | 12/1996 |

OTHER PUBLICATIONS

Bador, R. et al. Erythrosin as energy acceptor in a biphasic chemiluminescent system for glucose oxidase detection, 1991, Analytica Chimica Acta, vol. 251, pp. 215-222.*
O. M. Steijger et al.; "Chemiluminescence of bis (2,4,6-trichlorophenyl) Oxalate in Aqueous Micellar Systems"; vol. 217, Elsevier Science Publishers B.V., Amsterdam, 1989, pp. 229-237. Cited in the ISR.
International Search Report of PCT/JP2006/326295, date of mailing Jan. 30, 2007.

* cited by examiner

*Primary Examiner* — Yelena G Gakh
*Assistant Examiner* — Robert Xu
(74) *Attorney, Agent, or Firm* — Westerman, Hattori, Daniels & Adrian, LLP

(57) ABSTRACT

It is intended to provide a method whereby residual detergent (surfactant) can be conveniently and accurately detected in the step of washing or rinsing dishes or clothes, and a test device usable in examining the rinsed conditions. Namely, a method characterized by comprising bringing a test substance with a composition (test agent) comprising an oxalic acid ester, a fluorescent substance, hydrogen peroxide and a strong acid and thus easily detecting the residual detergent sticking to the surface of the test subject from the chemiluminescence thus caused; and a test device which is most suitable for storing the test agent as described above.

6 Claims, 4 Drawing Sheets

METHOD OF DETECTING RESIDUAL DETERGENT AND DEVICE FOR DETECTING RESIDUAL DETERGENT

TECHNICAL FIELD

The present invention relates to a method of conveniently and accurately detecting residual detergent (surfactant or alkaline component) and device for detecting residual detergent.

BACKGROUND ART

In general, suitable surfactants are used as detergents in food processing plants and for washing clothes and dishes in general household. The detergent used is washed away under running water, followed by drying. However, whether the residual detergent (surfactant) exists after drying has not been checked. The impact of the residual detergent on human body has been considered to be one of the factors that cause allergies. A simple method for detecting the presence of the residual detergent has thus been desired.

Japanese Unexamined Patent Application Publication No. 8-320315 describes a method of detecting a surfactant adhering on a surface of a specimen, comprising wiping a test portion of the specimen surface with a detecting medium to transfer the test portion to the detecting medium, bringing the detecting medium into contact with a medium containing a dye, and detecting the surfactant on the basis of changes in color tone of the dye caused by the presence of the surfactant. However, changes in color are often too subtle to identify with naked eye; moreover, the sensitivity has not been satisfactory.

The inventor of the present invention has found that a chemiluminescent liquid emits intense light when brought into contact with trace amounts of residual detergent, and made the present invention on the basis of the further studies. Patent Document 1: Japanese Unexamined Patent Application Publication No. 8-320315

DISCLOSURE OF INVENTION

Problems to be Solved by the Invention

An object of the present invention is to provide a method of conveniently and accurately detecting residual detergent (surfactant) and a device for detecting residual detergent.

Means for Solving the Problems

The object of the present invention described above can be achieved through the following features.

In a composition containing an oxalate, a fluorescent substance, hydrogen peroxide, and a strong acid, examples of the oxalate include bis(2,4,5-trichloro-6-carbobutoxyphenyl oxalate) and bis(2,4,5-trichloro-6-carbopentoxyphenyl oxalate).

Examples of the fluorescent substance include 9,10-bis (phenylethynyl)anthracene, 1-methoxy-9,10-bis(phenylethynyl)anthracene, perylene, 1,5-dichloro-9,10-bis(phenylethynyl)anthracene, 1,8-dichloro-9,10-bis(phenylethynyl) anthracene, rubrene, monochloro and dichloro-substituted 9,10-bis(phenylethynyl)anthracene, 5,12-bis(phenylethynyl) tetracene, 9,10-diphenylanthracene, 16,17-dihexyloxyviolanthrone, 2-methyl-9,10-bis-(phenylethynyl)anthracene, 9,10-bis-(4-methoxyphenyl)-2-chloroanthracene, 9,10-bis-(4-ethoxyphenyl)-2-chloroanthracene, 16,17-didecycloxyviolanthrone, LUMOGEN RED (a perylenedicarboxylmide fluorescent agent that emits red color), LUMOGEN YELLOW (a perylenedicarboxylmide fluorescent agent that emits yellow color), LUMOGEN ORANGE (a perylenedicarboxylmide fluorescent agent that emits orange color), 5,12-bis-(phenylethynyl)naphthacene, 5,6,11,12-tetraphenylnaphthacene, and mixtures of these.

In the present invention, among the fluorescent substances described above, those that emit blue color are effective. For example, a chemiluminescent composition containing a fluorescent substance, 9,10-bis-(4-ethoxyphenyl)-2-chloroanthracene (blue emission) is a transparent liquid under naked eye and that the liquid is not emitting light can be easily recognized with naked eye. However, if other fluorescent substances, such as those in yellow, green, and orange, are used, they develop illusion as if they emit light when observed in a poor light.

The strong acid used in the present invention may be an organic acid or an inorganic acid. The strong acid functions as a negative catalyst that suppresses the reaction of the oxalate with hydrogen peroxide. The organic strong acid is preferably an aromatic or fatty strong acid having a sulfonic acid group, a phosphoric acid group, or a carboxylic acid group. Examples of the aromatic sulfonic acid include benzene sulfonic acid and p-toluene sulfonic acid. Examples of the fatty sulfonic acid include methanesulfonic acid, ethanesulfonic acid, and methanedisulfonic acid. Examples of the inorganic strong acid include hydrobromic acid, hydrochloric acid, sulfuric acid, and nitric acid. In this invention, for example, 0.005 to 0.05% of sulfuric acid (about 95%) may be added to one of a composition (A) containing an oxalate, a fluorescent substance, and an organic solvent and a composition (B) containing hydrogen peroxide and an organic solvent, or a total of 0.005 to 0.05% of sulfuric acid may be added to both of the composition (A) and the composition (B).

In this invention, the composition (detecting agent) containing the oxalate, the fluorescent substance, hydrogen peroxide, and the strong acid is kept in non-emission state until it contacts with residual detergent. In order to do this, the strong acid is used to suppress reaction of the oxalate with hydrogen peroxide. In this manner, since emission from a test portion of a test subject that has not been emitting light at all can be identified with naked eye, emission can be easily recognized. Although this recognition is possible in a poor light, recognition is further facilitated in a light-shielded container. Examples of the solvent for the chemiluminescent composition of the present invention include acetyl tributyl citrate (ATBC), triethyl citrate, benzyl benzoate, butyl benzoate, dipropylene glycol dimethyl ether (DMM), and phthalates such as dimethyl phthalate and dibutyl phthalate. Moreover, tert-butanol and ethyl alcohol are preferred as the alcohol.

Although the above-described mixture of the oxalate, the fluorescent substance composition, hydrogen peroxide, and the strong acid has reaction suppressed, the suppression is not perfect and degradation tends to occur after four to five months. Thus, it is best to separately store the composition A containing the oxalate, the fluorescent substance, and the organic solvent and the composition B containing hydrogen peroxide and the organic solvent. The strong acid is added to one or both of the composition A and composition B.

The detection method of the present invention is effective for detecting various types of surfactants. Examples of the surfactants include cationic surfactants, anionic surfactants, nonionic surfactants, and amphoteric surfactants.

The composition A and the composition B are stored in separate containers, and immediately before testing, the composition in one container is transferred to the other for mixing.

A structure in which one of the compositions is charged in a flexible container and the other composition is charged in a breakable ampule contained in the flexible container so that immediately before testing, the flexible container can be bent to break the ampule inside and shaken so that the two compositions mix with each other is optimum as a convenient device for detecting residual detergent.

The detecting medium preferably has a shape of a cotton-tipped swab, such as a bar provided with a fibrous impregnating material 7 that does not cause chemiluminescent reaction with a testing agent (FIG. 6).

Advantages

According to the present invention, emission can be readily recognized with naked eye by directly applying or dropping the testing agent onto a test subject, and thus the presence or absence of residual detergent can be easily and conveniently identified. If the test subject is large in size or of a nature that does not allow direct application, a detecting medium is used for transfer and the medium is brought into contact with the detecting agent so that the residual detergent can be identified by emission.

REFERENCE NUMERALS

Figure 1:
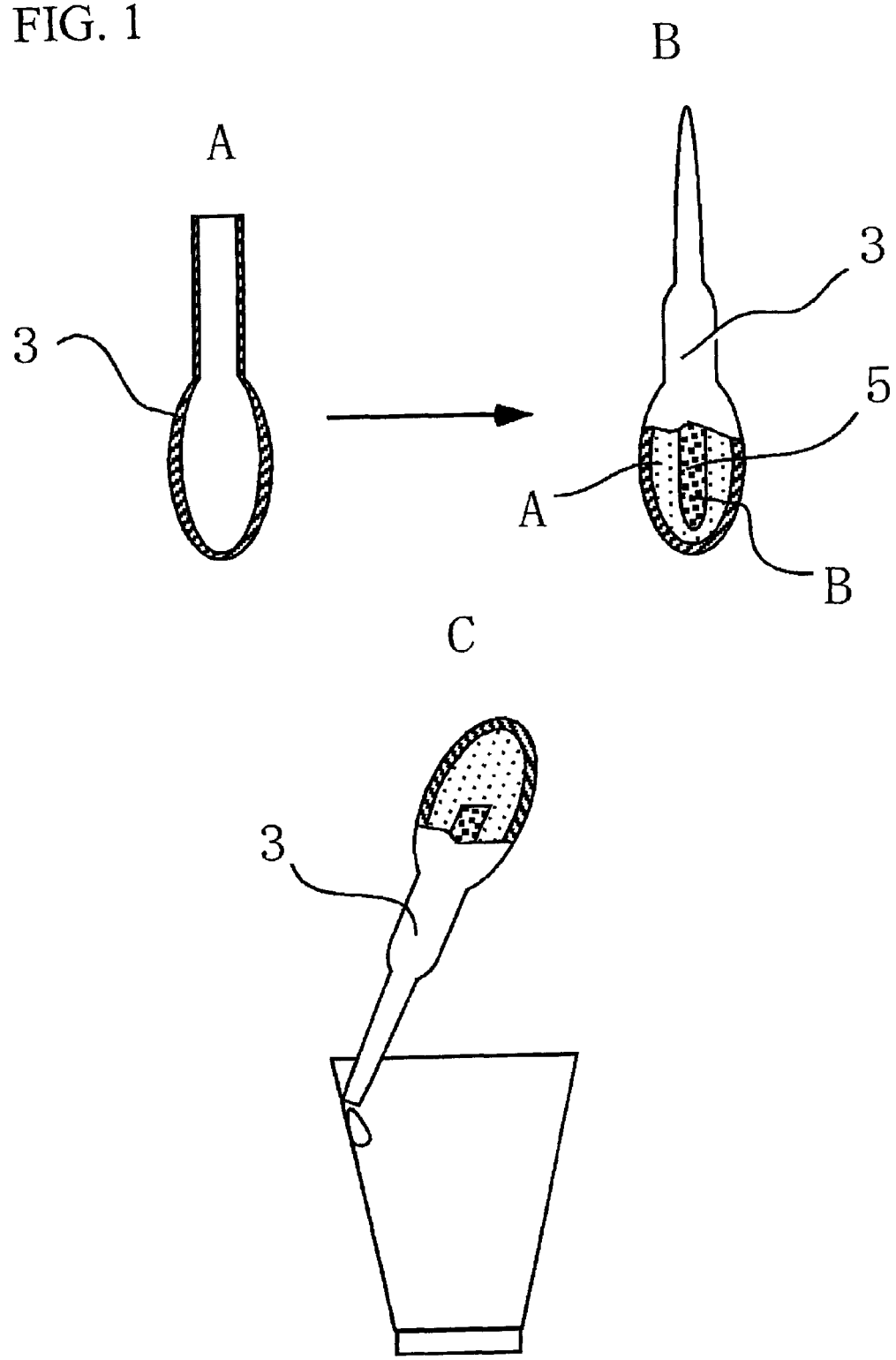
FIG. 1A is a cross-sectional view of a hollow container 3 of a device for detecting residual detergent of the present invention, B is a cross-sectional illustration of the device for detecting the residual detergent, and C is an illustration showing one example of a condition of use.
Figure 2:
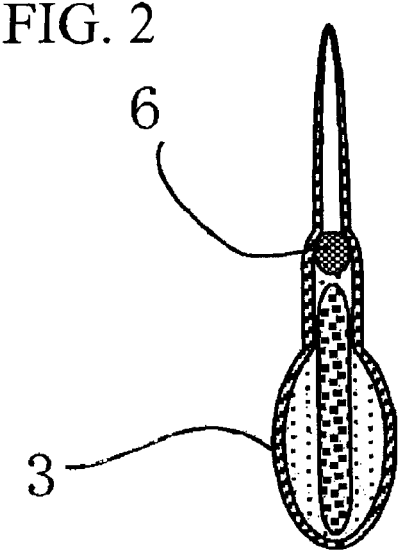
FIG. 2 is a cross-sectional view showing a filter 6 inserted into the device for detecting residual detergent of the present invention.

1: Composition A, 2: Composition B, 3: Hollow container, 4: Container having a cap with a nozzle, 5: Breakable ampule, 6: Filter, 7: Fibrous impregnating material

BEST MODES FOR CARRYING OUT THE INVENTION

The present invention will now be described in further detail by examples below.

Example 1

A solution containing 5 wt % of bis(2,4,5-trichloro-6-carbopentoxyphenyl oxalate) as the oxalate, 0.1 wt % of 9,10-bis-(4-ethoxyphenyl)-2-chloroanthracene as the blue fluorescent substance, and 94.69 wt % of ATBC as a solvent was prepared (composition A). A solution containing 3 wt % of hydrogen peroxide, 0.01 wt % of methanesulfonic acid as the organic strong acid, and 82.16 wt % of TEC and 14.38 wt % of ethanol as the solvent was prepared (composition B). The composition A was mixed with the composition B. The resulting solution was transparent and no emission phenomenon was observed.

The above-described testing agent was used to test the detergents produced by various manufacturers. The ratio of mixing the composition A to the composition B was 5:1.

The measurement procedure was as follows: 5 cc of the testing agent was placed in a test tube, and 0.6 cc of each of detergent solutions prepared by diluting detergents to 1000 ppm, 100 ppm, 10 ppm, and 1 ppm was added to the testing tube dropwise.

The state of emission was observed in a dark room.

| Trade name (manufacturer) | Type of surfactant | Product classification |
| --- | --- | --- |
| 1. Humming (Kao Corporation) | Cationic surfactant, amine salt type | Fabric softener |
| 2. Emal (Kao Corporation) | Nonionic surfactant, ether type | Laundry detergent |
| 3. Kitchen Kirei Kirei Jokin & Hyohaku (Lion Corporation) | Nonionic surfactant, amine alkylene oxide | Kitchen bleach |
| 4. Homing (Kao Corporation) | Nonionic surfactant, ether type | Cleanser |
| 5. More Excellent (Kao Corporation) | Nonionic surfactant, alkyl glycoside | Kitchen detergent |
| 6. Kitchen Haiter (Kao Corporation) | Anionic surfactant, sulfate | Kitchen bleach |
| 7. Power Plus Joy (P&G Far East, Inc.) | Anionic surfactant, sulfate and other components | Kitchen detergent |
| 8. Yashinomi Senzai (Saraya Co., Ltd.) | Anionic surfactant sulfate and other components | Kitchen detergent |
| 9. Shabondama Kitchen Soap Solid (Shabondama Soap Co.) | Anionic surfactant, carboxylate | Kitchen soap |
| 10. Murin Top (Lion Corporation) | Anionic surfactant, sulfonate | Laundry detergent |

Experimental Results by Observation with Naked Eye in a Dark Room

A: Strong emission, B: Emission, C: Weak emission, D: Very weak emission, E: No emission The results rated by the standard above are shown below:

| Trade name (manufacturer) | Concentration: 1000 ppm | Concentration: 100 ppm | Concentration: 10 ppm | Concentration: 1 ppm |
|---|---|---|---|---|
| 0. No detergent | E | E | E | E |
| 1. Humming (Kao Corporation) | A | B | C | E |
| 2. Emal (Kao Corporation) | C | E | E | E |
| 3. Kitchen Kirei Kirei Jokin & Hyohaku (Lion Corporation) | A | B | D | E |
| 4. Homing (Kao Corporation) | D | D | D | E |
| 5. More Excellent (Kao Corporation) | A | B | C | E |
| 6. Kitchen Haiter (Kao Corporation) | C | D | D | E |
| 7. Power Plus Joy (P&G Far East, Inc.) | C | D | E | E |
| 8. Yashinomi Senzai (Saraya Co., Ltd.) | E | E | E | E |
| 9. Shabondama Kitchen Soap Solid (Shabondama Soap Co.) | A | C | E | E |
| 10. Murin Top (Lion Corporation) | A | C | E | E |

In the experiment above, emission was observed in all detergent at a detergent concentration of 1000 ppm, except for Yashinomi Senzai. Very weak emission was observed for Homing. At a concentration of 100 ppm, no emission was observed from Emal and Yashinomi Senzai.

The surfactant components and other components of the individual products as far as could be investigated are described below:

| Trade name (manufacturer) | Surfactant component | Other component |
|---|---|---|
| 1. Humming (Kao Corporation) | Ester amide-type dialkyl amine salt | |
| 2. Emal (Kao Corporation) | Polyoxyethylene alkyl ether | Stabilizer, pH adjustor |
| 3. Kitchen Kirei Kirei Jokin & Hyohaku (Lion Corporation) | Alkyl amine oxide | Sodium hypochlorite, sodium hydroxide |
| 4. Homing (Kao Corporation) | Polyoxyethylene alkyl ether | Polishing agent |
| 5. More Excellent (Kao Corporation) | Alkyl glycoside | Stabilizer |
| 6. Kitchen Haiter (Kao Corporation) | Sodium alkyl ether sulfate | Sodium hypochlorite, sodium hydroxide |
| 7. Power Plus Joy (P&G Far East, Inc.) | Sodium alkyl ether sulfate, alkyl amine oxide, polyoxyethylene alkyl ether | Stabilizer, viscosity adjustor, enzyme |
| 8. Yashinomi Senzai (Saraya Co., Ltd.) | Sodium alkyl ether sulfate, fatty acid alkanol amide | |
| 9. Shabondama Kithen Soap Solid (Shabondama Soap Co.) | Fatty acid sodium salt | |
| 10. Murin Top (Lion Corporation) | Straight-chain sodium alkyl benzene sulfonate, alpha sodium sulfonate | Alkaline chemical (carbonate, silicate), water softener (alumino silicate), stabilizer (sulfate) |

Example 2

Experiments of Detecting Residual Detergent

1.

To 2000 cc of water, 1.5 cc of detergent was added, and the resulting mixture was stirred.

2.

The resulting liquid was impregnated in a sponge, and an inner surface of a glass cup was rubbed with the sponge times.

3.

Subsequently, running water (tap water) was poured into the cup until the cup is overfull, and then the cup was emptied. This was accounted as first rinsing. Second and third rinsing was then performed in the same manner. The cup was then placed in a drier to dry.

4.

A testing agent of Example 1 was dropped onto the inner surface of the cup.

5.

Whether emission occurred was observed in a poor light with naked eye.

6. The results when rinsing was performed by using warm water of 50° C. are also shown below.

|  | First rinsing | Second rinsing | Third rinsing |
|---|---|---|---|
| Tap water | | | |
| More Excellent | Emission | Emission | Weak emission |
| Power Plus Joy | Emission | Emission | Emission |
| Yashinomi Senzai | Emission | Emission | Weak emission |
| Charmy V Quick | Emission | Emission | Weak emission |
| Family Fresh | Emission | Emission | Weak emission |
| Warm water (50° C.) | | | |
| More Excellent | Weak emission | Weak emission | Below detectable level |
| Power Plus Joy | Weak emission | Weak emission | Weak emission |
| Yashinomi Senzai | Weak emission | Weak emission | Below detectable level |
| Charmy V Quick | Weak emission | Weak emission | Below detectable level |
| Family Fresh | Weak emission | Weak emission | Below detectable level |

In the examples above, the average results of testing three cups are indicated.

The results show that these commercially available detergents are not easy to wash off with water. It is also shown that although the detergent are more easily washed off with warm water, three times of rinsing are required to completely wash off the detergent.

Example 3

The relationship between the amount of residual detergent and the emission luminance was studied through experiments.

To 50 μl, 25 μl, and 5 μl of detergent, More Excellent, 50 ml, 25 ml, and 5 ml of tap water were respectively added to adjust the concentration to 1000 ppm. Each of the resulting mixture was placed in a thermostatic oven at 80° C. to dry. (Since the concentration was the same, the amount of tap water added increases with the amount of detergent.)

After each sample was left to stand at room temperature, 10 ml of the testing agent of Example 1 was added, and measurement was conducted after stirring.

The luminance meter was LS100 produced by Minolta Corporation, and the unit of measure was $mcd/m^2$ (the luminance meter and the units of measure below are also the same).

| Measurement results | | | |
|---|---|---|---|
| | Amount of detergent added | | |
| Trade name | 50 μl | 25 μl | 5 μl |
| More Excellent | 323 | 202 | 134 |

The results show that the level of luminance increases with the amount of residual detergent and can be used as the standard for understanding the amount of residual detergent in household and plants using the same detergents.

In this invention, it has been confirmed that the testing agent reacts with the minor components in the tap water and thereby emits light. If the level of emission caused by the minor components is high enough to be recognizable with naked eye, the testing becomes incomplete. Thus, the reaction must be suppressed to a degree that the emission is not recognizable. In view of the above, the optimum amount of the methanesulfonic acid was investigated.

Example 4

Reaction of Minor Component in Tap Water with Testing Agent

A testing agent was prepared by adjusting the concentration of methanesulfonic acid of Example 1 as below (A:B=5:1).

Into containers, 50 ml, 25 ml, and 5 ml of tap water was charged and dried at 80° C. To each dried container, 10 ml of the testing agent was added to measure emission.

| Concentration of methanesulfonic acid | Amount of water | | |
|---|---|---|---|
| | 50 ml | 25 ml | 5 ml |
| 0.001% | 116 | 35 | 15 |
| 0.005% | 17 | 9 | 9 |
| 0.01% | 6 | 6 | 6 |
| 0.015% | 7 | 5 | 2 |
| 0.02% | 5 | 3 | 3 |

In the case where methanesulfonic acid was used, the concentration at which no emission was recognized was about 0.01%; however, the concentration varies with the type of the organic strong acid used. Thus, the concentration is not particularly limited to this.

It should also be noted that the sensitivity of human eye to light differs from person to person. It can be assumed that the luminance at which blue light can be recognized in a poor light is about 30 $mcd/m^2$.

The following test was conducted next.

Three types of aqueous solutions with detergent (More Excellent) concentrations of 100 ppm, 10 ppm, and 1 ppm, respectively, were prepared with tap water. Glass cups were respectively immersed in the aqueous solutions, emptied, and dried. The testing agent of Example 1 was dropped onto the dried glass cups and the glass cups were observed with naked eye in poor light. Emission was confirmed from the 100 ppm and 10 ppm samples but emission from the 1 ppm could not be confirmed unless in a dark room.

Example 5

Measurement of Emission Luminance after Solution Containing 1000 ppm of Surfactant was Dried 1. Objective To measure the catalytic effects of anionic, cationic, nonionic, and nonionic surfactants for luminescent liquids.

2. Specimens

The surfactants produced by Dai-ichi Kogyo Seiyaku Co., Ltd., and indicated in Table 1 below were used as the surfactants.

Surfactants produced by Dai-ichi Kogyo Seiyaku Co., Ltd.

TABLE 1

| Product name | Surfactant type | Composition | Concentration |
|---|---|---|---|
| 1. Monogen T-423S | Anionic | Triethanolamine alkyl sulfate | 35% |
| 2. Hitenol 330T | Anionic | Sodium polyoxyethylene tridecyl ether sulfate (3E.O.) | 35% |
| 3. Neo-Hitenol L-30 | Anionic | Disodium polyoxyethylene lauryl sulfosuccinate | 25% |
| 4. Neocol YSK | Anionic | Dioctyl sodium sulfosuccinate | 70% |
| 5. Neo-Hitenol ECL-30S | Anionic | Sodium polyoxyethylene lauryl ether acetate | 27% |
| 6. Plysurf A208B | Anionic | Polyoxyethylene lauryl ether phosphoric acid | 99% |
| 7. Catiogen TMP | Cationic | Cetyltrimethylammonium chloride | 29% |
| 8. Catiogen BC-50 | Cationic | Benzalkonium chloride liquid | 50% |
| 9. Amogen S | Amphoteric | Betaine lauryldimethylaminoacetate | 32% |
| 10. Amogen AOL | Amphoteric | Lauryldimethylamine oxide liquid | 32% |
| 11. Noigen CL-200 | Nonionic | Special ether-type nonionic surfactant | 100% |
| 12. Noigen TDS-50 | Nonionic | Polyoxyethylene tridecyl ether | 100% |
| 13. Noigen TDS-200D | Nonionic | Polyoxyethylene tridecyl ether | 100% |
| 14. Dianol CDE | Nonionic | Coconut oil fatty acid diethanolamide | 100% |
| 15. Sorgen TW-80V | Nonionic | Polyoxyethylene sorbitane monooleate (20 E.O.) | 100% |

3.

Measurement Instrument

Luminance meter: MINOLTA LS-100

TABLE 2

| Luminescence liquid composition | | | |
|---|---|---|---|
| | | Chemical name | Conc. |
| Fluorescent liquid, oxalate | Oxalic acid ester CPPO | Bis[3,4,6-trichloro-2-(3-methylbutyloxycarbonyl)phenyl]oxalate | 0.123 mol/L |
| | Fluorescent substance 2-CIBEPA | 2-Chloro 9,10-Bis(4-ethoxy phenylanthracene) | 2.45 mmol/L |
| | Solvent | | |
| | ATBC | Acetyl tributyl citrate | 70 vol % |
| | BZB | Benzyl benzoate | 30 vol % |
| Oxidizing liquid, activator | Hydrogen peroxide Acid | Hydrogen peroxide Methanesulfonic acid | 3 wt % 1.5 mmol/L |
| | Solvent | | |
| | TEC | Triethyl citrate | 80 vol % |
| | ETOH | Ethanol | 20 vol % |

4.

Experiment Procedure (1) Each surfactant was diluted with water to a concentration of 25 wt %.

(2) From the 25% surfactant solution prepared as above, 25 μl was sampled and charged in a 100 ml beaker, and 25 ml of water was added to the beaker to adjust the concentration to ppm. The resulting mixture was thoroughly stirred.

(3) The beaker of (2) was placed in a thermostatic oven at 80° C. and dried until moisture was gone (1 day).

(4) The fluorescent liquid shown in Table 2 was mixed with an oxidizing liquid at a volume ratio of 5:1. The resulting liquid (10 ml) was poured into the beaker dried in (3) and thoroughly stirred.

(5) The emission luminance of the luminance liquid 1 minute and 10 minutes after the liquid was poured into the beaker was measured.

(6) Samples with weak emission were readjusted so that the concentration in (2) was increased to 5000 ppm and 10000 ppm and were subjected to the operations of (3) and onward to measure the emission luminance.

5.

Experimental Results

Emission could be confirmed from all surfactants. However, some surfactants showed weak catalytic effects for emission. However, emission could be confirmed by increasing the concentration to 10000 ppm. The results show that the surfactants used in the experiment have catalytic effects although there are differences in reactivity for luminescence liquids depending on the type of the surfactant.

1 to 6: Anionic surfactants
7 to 8: Cationic surfactants
9 and 10: Amphoteric surfactants
11 to 15: Nonionic surfactants
E=No emission, D=very weak emission, C=weak emission, B=emission, A=intense emission

TABLE 3

| Test specimens | Surfactant concentration: 1000 ppm | | | | | | | | |
|---|---|---|---|---|---|---|---|---|---|
| | Emission luminance [mcd/m$^2$] | | | | | | Emission observed with naked eye | | |
| | After 1 min | | | After 10 min | | | | | |
| | First | Second | Third | First | Second | Third | After 1 min | After 10 min | pH |
| Blank | 3 | 2 | 3 | 1 | 1 | 1 | E | E | |
| 1. Monogen T-423S | 2 | 1 | 3 | 4 | 1 | 2 | E | E | 7.1 |
| 2. Hitenol 330T | 23 | 15 | 22 | 15 | 11 | 13 | D | D | 8.5 |
| 3. Neo-Hitenol L-30 | 111 | 186 | 123 | 20 | 25 | 18 | C | D | 5.5 |
| 4. Neocol YSK | 316 | 289 | 302 | 267 | 255 | 234 | B | B | 7.1 |
| 5. Neo-Hitenol ECL-30S | 27390 | 23180 | 24520 | 7148 | 6982 | 8310 | A | B | 6.1 |
| 6. Plysurf A208B | 10 | 19 | 17 | 383 | 265 | 118 | D | B | 1.3 |
| 7. Catiogen TMP | 2 | 3 | 3 | 8746 | 7986 | 6548 | E | B | 6.9 |
| 8. Catiogen BC-50 | 14500 | 130210 | 14370 | 8 | 3 | 6 | A | E | 8.6 |
| 9. Amogen S | 1270 | 1140 | 1223 | 523 | 438 | 521 | B | B | 5.6 |
| 10. Amogen AOL | 25 | 18 | 20 | 3 | 2 | 5 | D | E | 7.8 |
| 11. Noigen CL-200 | 10500 | 10300 | 14160 | 4010 | 3289 | 4105 | A | B | 8.0 |
| 12. Noigen TDS-50 | 15 | 18 | 10 | 26 | 18 | 15 | D | D | 6.2 |
| 13. Noisgen TDS-200D | 14 | 13 | 12 | 5 | 3 | 5 | D | E | 6.4 |
| 14. Dianol CDE | 3 | 1 | 5 | 5 | 1 | 5 | E | E | 9.8 |
| 15. Sorgen TW-80V | 10 | 12 | 15 | 3 | 5 | 3 | D | E | 9.7 |

TABLE 4

| Test specimens | Surfactant concentration: 5000 ppm | | | | | | | |
|---|---|---|---|---|---|---|---|---|
| | Emission luminance [mcd/m$^2$] | | | | | | Emission observed with naked eye | |
| | After 1 min | | | After 10 min | | | | |
| | First | Second | Third | First | Second | Third | After 1 min | After 10 min |
| Blank | 3 | 2 | 3 | 1 | 1 | 1 | E | E |
| 1. Monogen T-423S | 2 | 1 | 3 | 4 | 1 | 2 | E | E |
| 10. Amogen AOL | 14140 | 14500 | 15000 | 10 | 9 | 13 | A | D |
| 14. Dianol CDE | 3 | 1 | 5 | 5 | 1 | 5 | E | E |

TABLE 5

| Test specimens | Surfactant concentration: 1000 ppm | | | | | | | |
|---|---|---|---|---|---|---|---|---|
| | Emission luminance [mcd/m$^2$] | | | | | | Emission observed with naked eye | |
| | After 1 min | | | After 10 min | | | | |
| | First | Second | Third | First | Second | Third | After 1 min | After 10 min |
| Blank | 3 | 2 | 3 | 1 | 1 | 1 | E | E |
| 1. Monogen T-423S | 3 | 3 | 2 | 50 | 55 | 53 | E | D |
| 14. Dianol CDE | 647 | 653 | 686 | 233 | 254 | 210 | B | B |

Names in English of the surfactants described above used in INCI are as shown below.

| Product name | Chemical name | Other names or INCI codes |
| --- | --- | --- |
| 1. Monogen T-423S | Triethanolamine alkyl sulfate | TEA alkyl(C12, 13) sulfate |
| 2. Hitenol 330T | Sodium polyoxyethylene tridecyl ether sulfate (3E.O.) | Sodium trideceth sulfate |
| 3. Neo-Hitenol L-30 | Disodium polyoxyethylene lauryl sulfosuccinate | Disodium laureth sulfosuccinate |
| 4. Neocol YSK | Dioctyl sodium sulfosuccinate | Dioctyl sodium sulfosuccinate |
| 5. Neo-Hitenol ECL-30S | Sodium polyoxyethylene lauryl ether acetate | Sodium laureth-4 acetate |
| 6. Plysurf A208B | Polyoxyethylene lauryl ether phosphoric acid | Laureth-2 phospahate |
| 7. Catiogen TMP | Cetyltrimethylammonium chloride | Cetrimonium chloride |
| 8. Catiogen BC-50 | Benzalkonium chloride liquid | Benzalkonium chloride |
| 9. Amogen S | Betaine lauryldimethylaminoacetate | Lauryl betaine |
| 10. Amogen AOL | Lauryldimethylamine oxide liquid | Lauramine oxide |
| 11. Noigen CL-200 | Special ether-type nonionic surfactant | |
| 12. Noigen TDS-50 | Polyoxyethylene tridecyl ether | Trideceth-5 |
| 13. Noigen TDS-200D | Polyoxyethylene tridecyl ether | Trideceth-20 |
| 14. Dianol CDE | Coconut oil fatty acid diethanolamide | Cocamide DEA, glycerin |
| 15. Sorgen TW-80V | Polyoxyethylene sorbitane monooleate (20 E.O.) | Polysolvate 80 |

| INCI: International Nomenclature of Cosmetic Ingredient | |
| --- | --- |
| Product name | Chem/Other name or INCI |
| 1. Monogen T-423S | Tri ethanol almine alkyl(C12, 13) sulfate, water |
| 2. Hitenol 330T | Sodium trideceth sulfate, water |
| 3. Neo-Hitenol L-30 | Disodium laureth sulfosuccinate, water |
| 4. Neocol YSK | Dioctyl sodium sulfosuccinate, water, isopropyl alcohol |
| 5. Neo-Hitenol ECL-30S | Sodium laureth-4 acetate, water |
| 6. Plysurf A208B | Laureth-2 phospahate |
| 7. Catiogen TMP | Cetrimonium chloride, water |

A device for detecting residual detergent will now be described.

Into a hollow container 3 (FIG. 1A) having flexibility and a pointed portion shown in FIG. 1 and containing a glass ampule 5, a composition A containing an oxalate, a fluorescent substance, and an organic solvent is charged. Into the glass ampule, a composition B containing hydrogen peroxide, an organic strong acid, and an organic solvent is charged and sealed. Note that the hollow container 3 is composed of polyethylene and formed by blowing. Subsequently, the neck portion of the hollow container 3 was stretched under heating so as to seal the pointed portion (FIG. 1B). In use, the entire structure is bent to break the glass ampule inside so as to mix the composition A with the composition B. Then the pointed tip portion was cut to form an opening, and a flexible bulged portion of the hollow container 3 was pressed to drop the content onto a test subject (FIG. 1C).

Figure 3:
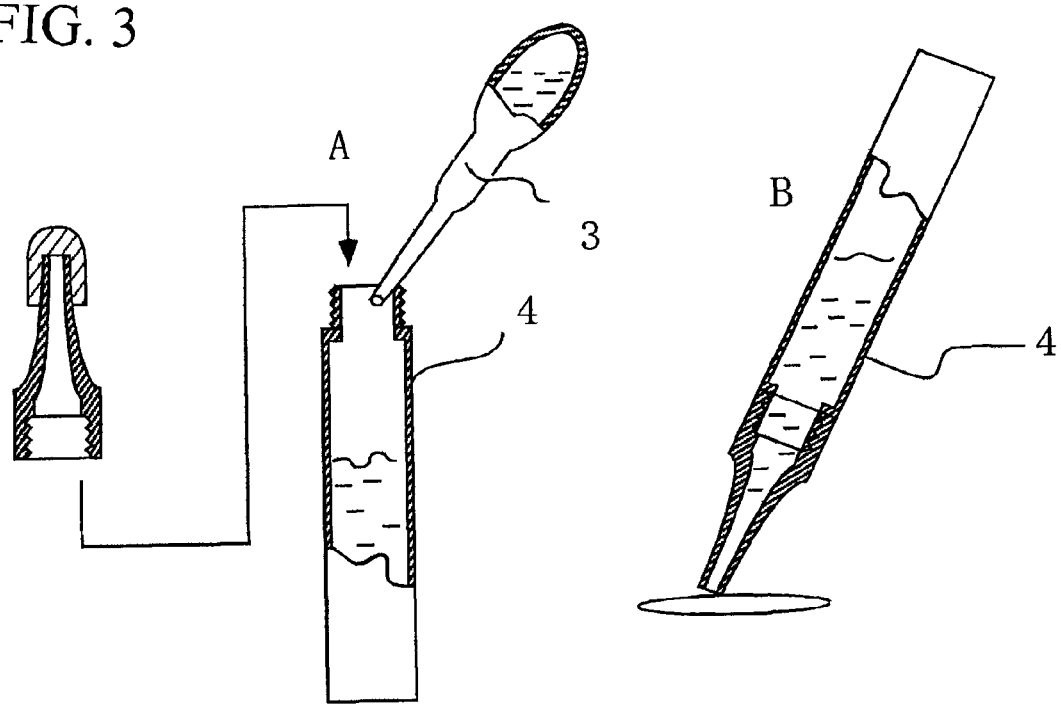
FIG. 3 is an illustration showing placing one of compositions A and B in a hollow container, placing the other composition in a hollow container having a cap with a nozzle, and discharging the one in the hollow container into the hollow container having the cap with the nozzle so as to mix the two compositions.
Figure 4:
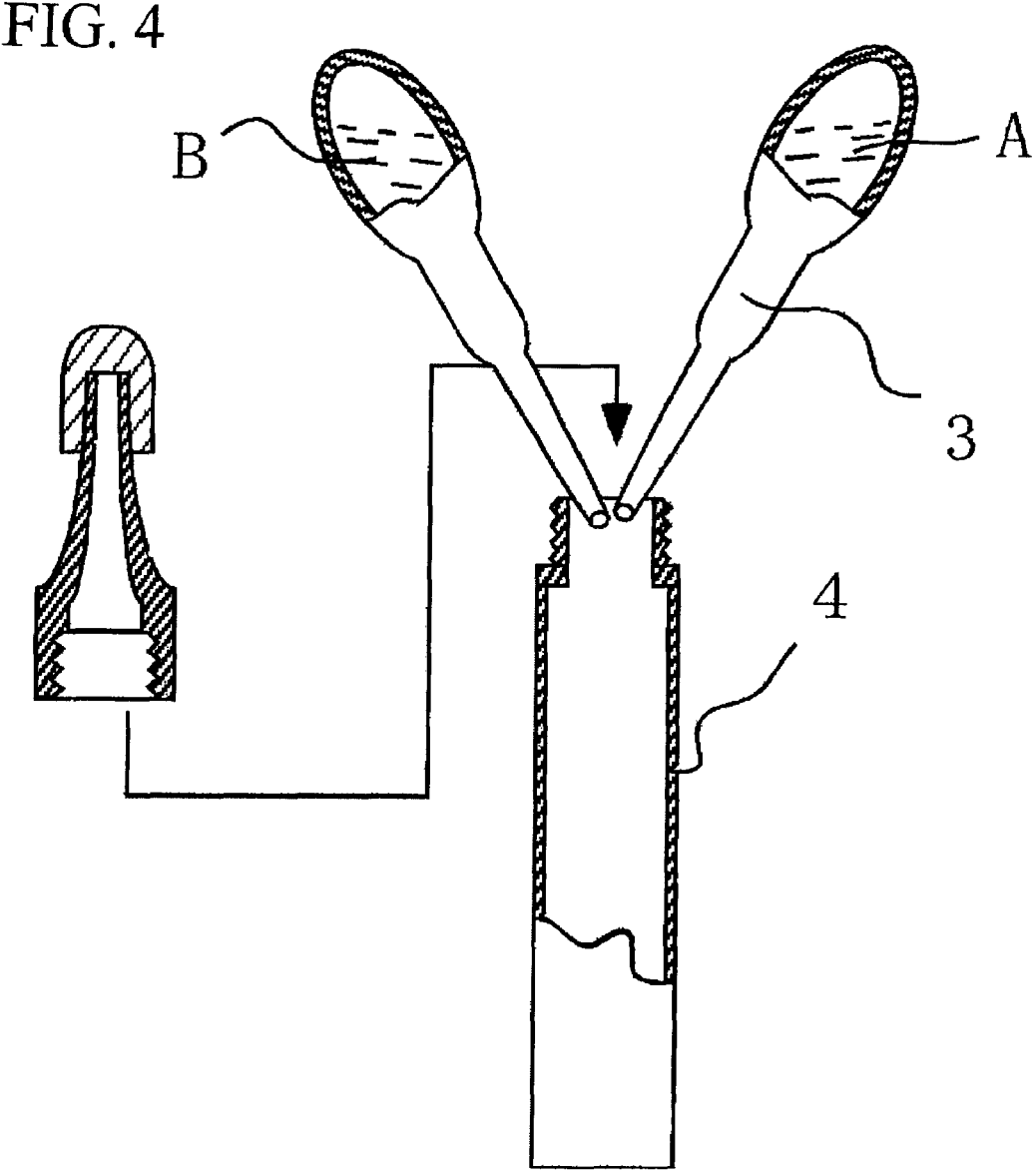
FIG. 4 is an illustration showing two hollow containers, in which one of compositions A and B is charged and sealed in one of the hollow containers, the other composition is charged and sealed in the other hollow container, and the compositions A and B are charged into another container having a cap with a nozzle from end openings of the two containers so as to mix the two compositions.
Figure 5:
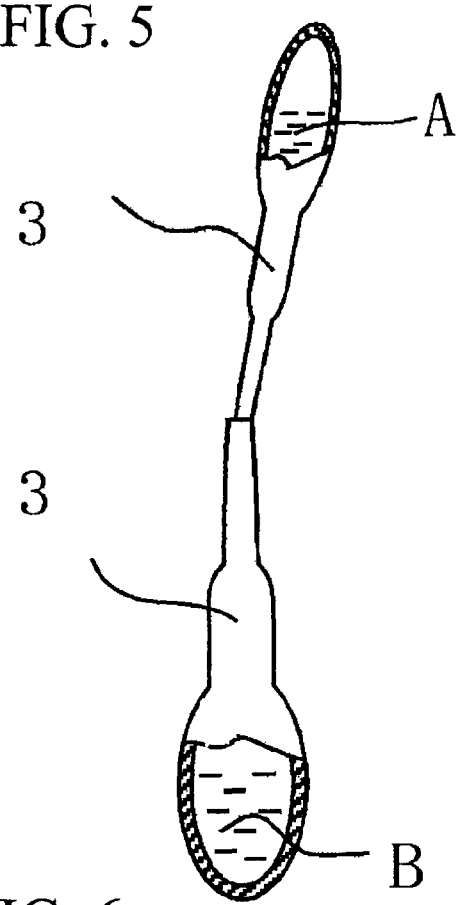
FIG. 5 is an illustration showing two hollow containers each having a pointed portion, in which one of compositions A and B is charged and sealed in one of the hollow containers, the other composition is charged and sealed in the other hollow container, and ends of the pointed portions of the hollow containers are opened so that the composition in one of the hollow container is charged into the other hollow container to mix the two compositions.
Figure 6:
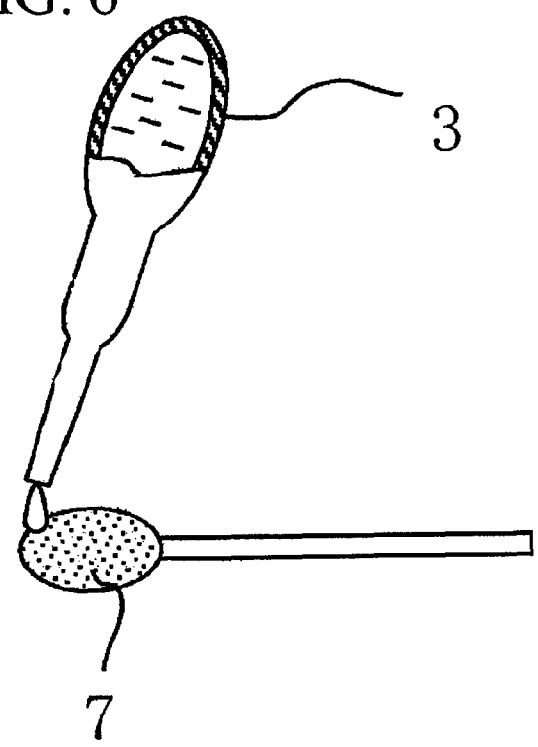
FIG. 6 is an illustration of a testing medium of the present invention.

FIGS. 3 and 5 show examples in which the composition A and the composition B are stored in separate containers. The composition in one container may be transferred to the other container to conduct mixing or the composition A and the composition B may be transferred to another container having a cap with a nozzle to conduct mixing, as shown in FIG. 4. The method for mixing is not limited to these as long as the compositions are stored separately.

INDUSTRIAL APPLICABILITY

According to the present invention, emission can be readily recognized with naked eye by directly applying or dropping the testing agent onto a test subject, and thus the presence or absence of residual detergent can be easily and conveniently identified.

The invention claimed is:

1. A method of detecting detergent adhering on a surface of a test subject, comprising:
preparing a composition comprising an oxalate, a fluorescent substance, hydrogen peroxide, and a strong acid, the composition containing strong acid sufficient to inhibit the chemiluminescence in an absence of a surfactant;
bringing the detergent adhering on a surface of the test subject into contact with the composition; and
monitoring chemiluminescence, thereby detecting residual detergent.

2. The method of detecting detergent, according to claim 1, wherein the fluorescent substance is capable of emitting blue light by the chemiluminescence.

3. The method of detecting detergent according to claim 1, wherein the step of bringing the test subject into contact with a composition comprises directly applying or dropping the composition on the test subject and the chemiluminescence occurs on the surface onto which the composition is applied or a portion onto which the composition is dropped.

4. The method of detecting detergent according to claim 1, wherein the step of bringing the test subject into contact with the composition comprises wiping a test portion of the test subject with a detecting medium so as to transfer the detergent adhering on a surface of the test portion onto the detecting medium.

5. The method of detecting detergent according to claim 1, the monitoring of chemiluminescence is carried out with naked eye.

6. The method of detecting detergent according to claim 4, wherein the detecting medium comprises a fibrous member impregnated with the composition.

* * * * *